(12) United States Patent
Cuppen

(10) Patent No.: US 6,259,766 B1
(45) Date of Patent: Jul. 10, 2001

(54) COMPUTER TOMOGRAPHY DEVICE

(75) Inventor: Johannes J. M. Cuppen, Eindhoven (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/212,628

(22) Filed: Dec. 16, 1998

(30) Foreign Application Priority Data

| Dec. 16, 1997 | (EP) | 97203963 |
|---|---|---|
| Oct. 28, 1998 | (EP) | 98203649 |
| Oct. 28, 1998 | (EP) | 98203651 |

(51) Int. Cl.[7] ................................................ G21K 1/04
(52) U.S. Cl. ........................... 378/147; 378/19; 378/98.8
(58) Field of Search ................................ 378/4, 19, 147, 378/98.8

(56) References Cited

U.S. PATENT DOCUMENTS

| 4,965,726 | * | 10/1990 | Heuscher et al. | 378/19 |
| 5,262,946 | * | 11/1993 | Heuscher | 378/15 |
| 5,430,784 | * | 7/1995 | Ribner et al. | 378/19 |
| 5,583,903 | * | 12/1996 | Saito et al. | 378/19 |
| 5,802,138 | * | 9/1998 | Glasser et al. | 378/19 |

FOREIGN PATENT DOCUMENTS

| 0365301A1 | 4/1990 | (EP) | A61B/6/03 |
| 0429977A2 | 11/1990 | (EP) | H05G/1/64 |
| WO98/05980 | 2/1998 | (WO) | G01T/1/29 |

* cited by examiner

Primary Examiner—Robert H. Kim
Assistant Examiner—Drew A. Dunn
(74) Attorney, Agent, or Firm—John F. Vodopia

(57) ABSTRACT

The computer tomography device includes an X-ray source for emitting an X-ray beam and a detector system for measuring density profiles of cross-sections of an object. The detector system includes a two-dimensional matrix of detector elements. The detector elements positioned along a direction transversely of the cross-sections have the same effective surface and detector elements positioned parallel to the cross-sections have different effective surfaces. Furthermore, the computer tomography device includes an adjustable X-ray collimator for limiting the X-ray beam transversely of the cross-sections.

6 Claims, 2 Drawing Sheets

COMPUTER TOMOGRAPHY DEVICE

BACKGROUND OF THE INVENTION

1. Field of the Invention

The invention relates to a computer tomography device which includes an X-ray ray source for emitting an X-ray beam and a detector system for picking up density profiles of cross-sections of an object to be examined.

2. Description of Related Art

A computer tomography device of this kind is known from the article "Computed tomography scanning with simultaneous patient translation" by Carl R. Crawford and Kevin F. King in Medical Physics 17 (1990), 967–982.

Computer tomography involves the formation of images of cross-sections of the object to be examined, for example a patient to be radiologically examined. To this end, the patient is irradiated by means of X-rays from different directions and, due to local differences in the X-ray absorption within the patient, density profiles are formed for the various directions, said profiles being measured by the detector system. To this end, the X-ray source and the detector system are rotated about the patient. An image representing the density of the patient in a cross-section is derived from the various density profiles. It is usually necessary to form a plurality of images of cross-sections along different, usually parallel planes. Such an operation is also referred to as volume scanning. In the known computer tomography device the patient is then displaced in the longitudinal direction with respect to the X-ray source and the detection system while being exposed to X-rays from different directions. The patient is preferably displaced at a uniform speed so as to ensure that the patient does not become "car sick" during the measurement of the density profiles.

The density profiles measured have not been picked up in a fixed longitudinal position; because the patient is displaced while the direction wherefrom the density profiles are measured changes, the longitudinal position varies as a function of the direction within the density profiles. The density profiles are measured along an approximately helical path, the pitch of the helix being constant when the patient is displaced in the longitudinal direction at a uniform speed. The axis of the helical path extends in the longitudinal direction. The known computer tomography device includes a data processing unit for deriving computed density profiles from the measured density profiles, the computed density profiles always relating to a slice through the patient in a given longitudinal position. The reconstruction unit utilizes the computed density profiles for a given longitudinal position so as to derive an image of the cross-section therefrom for the relevant longitudinal position.

SUMMARY OF THE INVENTION

It is an object of the invention to provide a computer tomography device which enables volume reconstruction to be performed faster and more accurately than by means of the known computer tomography device. It is another object of the invention to provide a computer tomography device for fast and accurate volume reconstruction while using only a limited number of individual detector elements.

This object is achieved by means of a computer tomography device according to the invention which includes an X-ray source for emitting an X-ray beam and a detector system for picking up density profiles of cross-sections of an object to be examined, which detector system includes a plurality of X-ray sensitive detector elements which are arranged in a two-dimensional pattern, in which detector elements in different positions along a transverse direction, parallel to the cross-sections, have substantially the same effective cross-section whereas at least some of the detector elements in different positions along a longitudinal direction, transversely of the cross-sections, have different effective cross-sections, and an X-ray collimator for spatially limiting the X-ray beam in the longitudinal direction, and substantially equal surface areas of detector groups, consisting of detector elements and/or parts of detector elements situated along the transverse direction, can be reached by the limited X-ray beam.

The computer tomography device according to the invention essentially enables simultaneous measurement of density profiles of individual cross-sections by means of the individual detector groups. Consequently, only a small amount of time is required to measure the density profiles of a substantial volume of the patient to be examined. Each of the density profiles represents density values in a cross-section of the patient to be examined. The individual cross-sections always relate to a part of the patient to be examined for the relevant, essentially the same longitudinal positions. Mathematically speaking this means that the cross-sections are planes at fixed longitudinal positions. The transverse direction extends perpendicularly to the longitudinal direction, so parallel to the cross-sections. It is not necessary to compute density profiles by interpolation: for individual cross-sections density values are measured for the longitudinal position of the relevant cross-section. Because density profiles are measured for the relevant longitudinal position, it is not necessary to compute these density profiles so that more accurate values can be obtained for the density profiles. Moreover, no time is wasted on carrying out the computations.

The respective detector groups of detector elements which have the same longitudinal positions and are reached by the X-rays over substantially the same surface areas pick up density values of essentially parallel cross-sections of the patient to be examined. From the incident X-rays, the individual detector elements derive a detector signal whose signal level represents the intensity of the incident X-rays. In order to ensure that substantially the same surfaces areas of detector elements of one and the same detector group are reached by X-rays, parts of detector elements are shielded by the X-ray collimator if the surface area of a relevant detector element per se is larger than the surface area to be reached, or detector signals of individual detector elements are combined when the surface area of the relevant detector elements that is reached by the X-rays is smaller than the surface area to be reached. Because reached surface areas of substantially the same size are formed by partly shielding detector elements, it is achieved that the density profiles are measured with a high spatial resolution despite the use of comparatively large detector elements. The resolution is determined by the effective surface area of the smallest effective surface area of the detector elements. Using a computer tomography device according to the invention, simultaneous measurement of density profiles of a larger part of the patient to be examined requires a number of detector elements which increases less than linearly as a function of the ratio of the smallest effective surface area to the linear dimension of the part of the patient for which density profiles are simultaneously measured. It is thus achieved that as a volume scan is made of a larger part of the patient in one operation, comparatively fewer additional, expensive detector elements will be required.

The detector system may be provided, for example with a sensor matrix with semiconductor photodiodes which are sensitive to X-rays and are connected to read-out lines via thin-film transistors per column. The gate contacts of the thin film transistors are connected to the addressing lines per row. Addressing signals, supplied via the addressing lines, open thin film transistors per row so as to read-out electric charges generated by the X-rays in the photodiodes in the relevant row. Said electric charges are thus read out via the read-out lines. An electronic multiplexer converts the electric charges read into an electric signal which represents the density profiles.

An alternative detector system comprises a plurality of detector elements. The detector elements include respective scintillators and photosensors. The scintillators convert X-rays in a low-energy radiation such as visible light, ultraviolet radiation or infrared radiation. The photosensors, such as photodiodes and phototransistors are sensitive for the low-energy radiation from the scintillator. The photosensors derive an electronic signal, such as an electric current or an electric voltage, from the low-energy radiation from the scintillators. Further the detector elements are provided with respective amplifiers which amplifies the electronic signal from the respective photosensors. Preferably, in the photosensors and their respective associated amplifiers are integrated in semiconductor technology, such as C-MOS on a substrate. In one embodiment of the detector system, the amplifiers are placed in the separate detector elements adjacent to the respective photosensors of which the amplifier amplifies the electronic signal . In another embodiment of the detector system the amplifiers are placed on the boundary of the substrate. The integration of the photosensors and the amplifiers on the same substrate achieves that the parasitic capacitances of the electrical lines that connect the photosensors to the amplifiers are reduced, so that the electrical noise level of the electronic signals that are applied to the amplifiers is reduced. The amplifiers can more specifically be charge sensitive capacitive feedback amplifiers. Such a charge sensitive capacitive feedback amplifier collects electric charge on a feedback capacitor during subsequent integration period and is reset by discharging the feedback capacitor after each integration period. The amplifiers can alternatively be transimpedance amplifiers. Such integrate the input photocurrent from the relevant photosensor and are continuously discharged. Both charge sensitive capacitive feedback amplifiers and transimpedance amplifiers have a wide dynamic range and are have a highly linear characteristic. Thus, these amplifiers generate amplified electronic signals which have a low noise level and hardly any non-linear distortion, so that these amplified electronic signals can be employed to display the image information with a high diagnostic quality. An electronic multiplexer converts the amplified electric signals into an electric signal which represents the density profiles.

For individual adjustments of the X-ray collimator it is possible to select substantially parallel cross-sections, having selectable transverse dimensions, for which density profiles are simultaneously measured. It is thus achieved that the dimensions of the part of the patient to be examined for which a volume scan is to be performed in one operation and the spatial resolution are selected by simple adjustment of the X-ray collimator. Consequently, a computer tomography device according to the invention is suitable for use for a wide variety of different radiological examinations. Moreover, the computer tomography device can be readily adjusted for the various examinations. Correct adjustment requires a short time only and no highly trained staff.

Because adjustment is simple and not very time consuming, it is also possible to change the adjustment in respect of the region to be examined and the spatial resolution during the radiological examination. This makes the computer tomography device according to the invention particularly suitable for performing volume scanning during a surgical operation such as an interventional procedure.

BRIEF DESCRIPTION OF THE DRAWING

These and other aspects of the invention will be described in detail hereinafter on the basis of the following embodiments and with reference to the accompanying drawing, in which.

DETAILED DESCRIPTION OF THE PREFERRED EMBODIMENT

Figure 1:
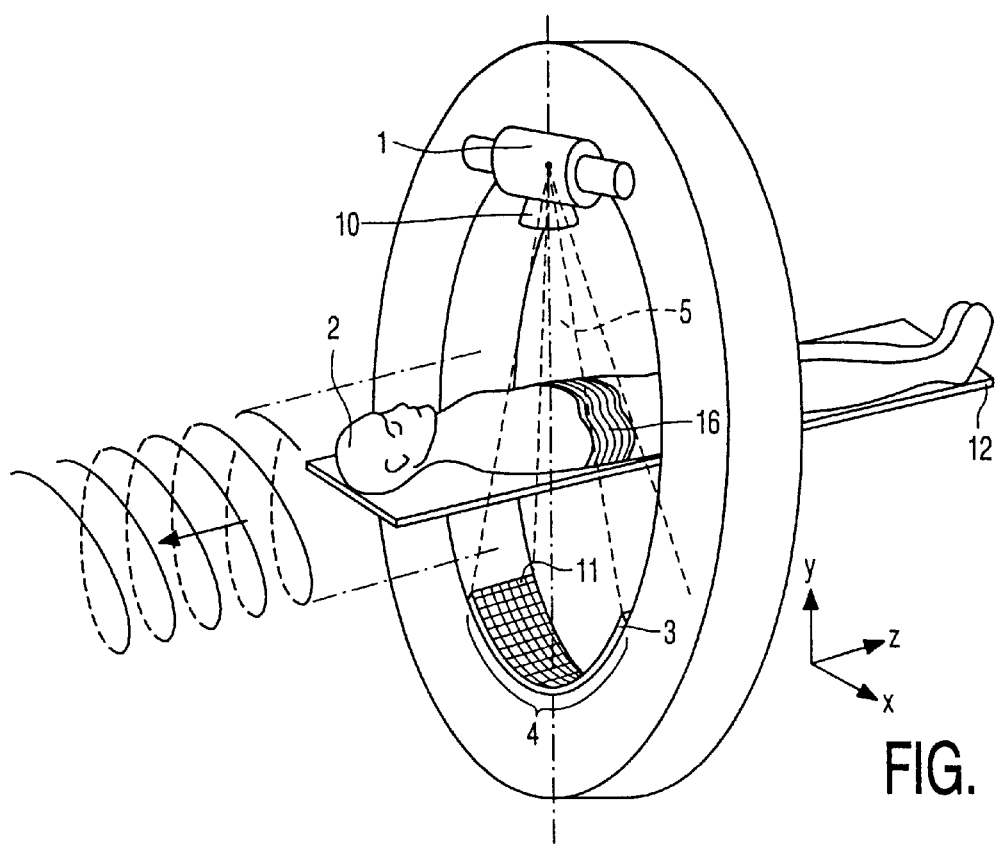
FIG. 1 is a three-dimensional diagrammatic representation of a computer tomography device according to the invention.
Figure 2:
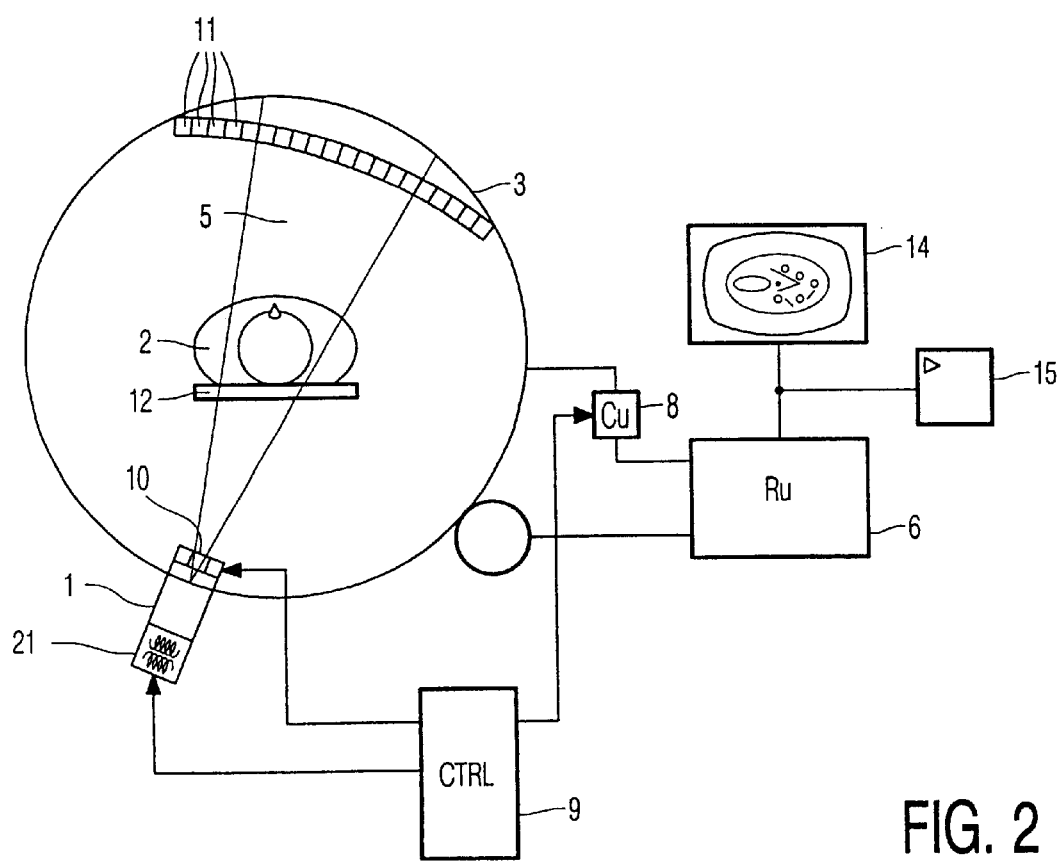
FIG. 2 shows diagrammatically a computer tomography device according to the invention.

FIG. 1 is a three-dimensional diagrammatic representation of a computer tomography device according to the invention. FIG. 2 shows diagrammatically a computer tomography device according to the invention. In co-operation with an adjustable X-ray collimator, an X-ray source 1 produces a diverging, essentially cone-shaped X-ray beam for irradiating the object 2, for example a patient to be examined. The detector system 3 is arranged so as to face the X-ray source 1. The X-ray collimator 10 is constructed as a slit-shaped diaphragm 10 with a slit whose dimensions can be adjusted. The thickness of the cone-shaped X-ray beam generally amounts to from 10 mm to 100 mm, measured halfway between the X-ray source and the detection system. The intensity of the radiation having passed the patient and incident on the detector system is determined predominantly by the absorption within the patient 2 who is arranged on a table 12 between the X-ray source and the detector system. By rotating the X-ray source 1 and the detector system 3 together about the patient by means of a frame 13, the absorption is measured along a large number of lines from a large number of directions. The common rotation of the X-ray source and the detection system may be continuous, but also intermittent. Furthermore, an annular anode arranged around the patient can also be used as the X-ray source, the target spot of an electron beam whereby X-rays are generated from the anode material then moving around the patient together with the annular anode. The computer tomography device includes a control unit 9 for adjusting the X-ray collimator. The control unit 9 adjusts the X-ray collimator electronically, for example on the basis of the type of radiological examination. The control unit 9 also adjusts the combination unit 8 in order to ensure that the density profiles are formed in conformity with the adjustment of the X-ray collimator. The control unit 9 also adjusts the high-voltage generator 21 in order to control the intensity and the energy of the X-rays. The detector system of the present embodiment is a position-sensitive detector system which includes a two-dimensional matrix of detector elements in the form of separate detector cells which are assembled in individual detector groups 4.

The detector cells 11 are, for example gas-filled (xenon) detectors or solid-state detectors.

Detector cells in the same detector group always have essentially the same effective cross-section for X-ray absorption. The detector system thus delivers absorption data from a significant three-dimensional volume of the patient by simultaneously measuring non-overlapping density profiles of a plurality of essentially parallel cross-sections through the patient to be examined. These cross-sections are measured along parallel slices 16 of the body of the patient by the individual detector groups 4 (single slice modes). The detector groups extend in the transverse direction, parallel to the cross-sections whose density profiles are being measured. The density profiles measured are used to form images of cross-sections of the patient 2. The signals from the detector cells 11 are applied to a combination unit 8 whereby the signals from the individual detector cells are combined so as to form signals representing the density profiles. To this end, the density profiles are applied to a reconstruction unit 6 which derives images from the density profiles of the respective cross-sections. The reconstruction unit performs a mathematical Radon transformation on the data values of the density profiles so as to derive the brightness values of the images therefrom. The reconstruction unit supplies image signals for the images, for example electronic video signals whose signal levels represent the brightness levels of the images. The image signals are applied to a monitor 14 on which the images of the cross-sections are simultaneously or consecutively displayed. It is alternatively possible to apply the image signals to a buffer unit 15 in which the image information is stored while awaiting further image processing, if any, or printing of a hard copy.

Figure 3:
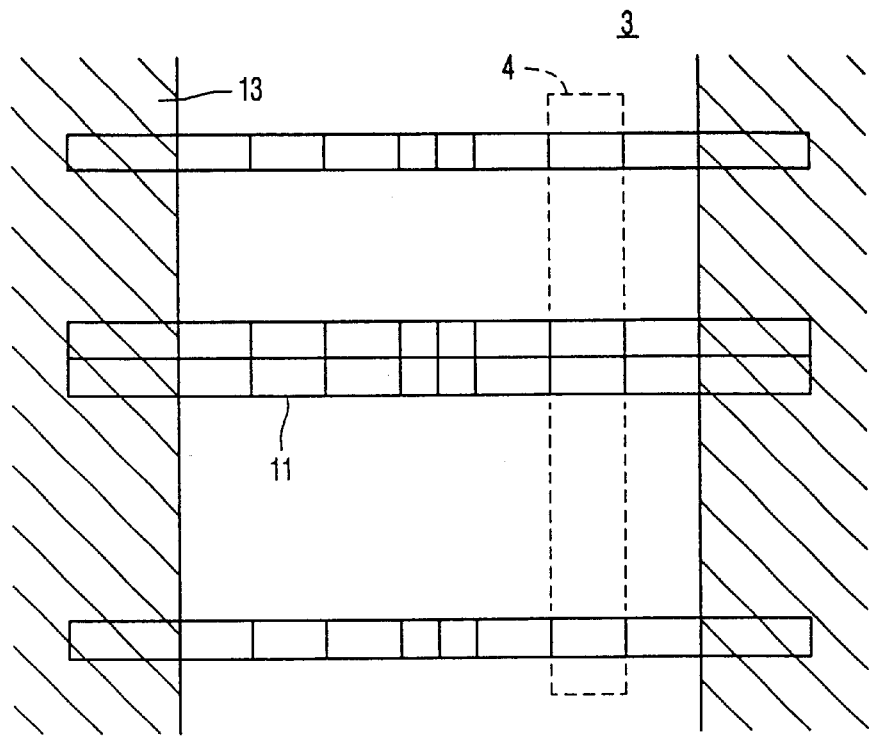
FIGS. 3 and 4 are diagrammatic views of the detector system of the computer tomography device according to the invention, looking in the direction from the X-ray source, with different adjustments of the X-ray collimator to generate multi-slice modes with non-overlapping profiles.

FIG. 3 is a diagrammatic view, looking in the direction from the X-ray source, of the detector system of the computer tomography device according to the invention while using a first adjustment of the X-ray collimator. The detector system includes a two-dimensional matrix of detector cells of which the extreme rows of detector cells and two further, arbitrary neighboring rows of detector cells are explicitly shown. In the present example the detector system is arranged in the computer tomography device in such a manner that its rows extend in the transverse direction and its columns extend in the longitudinal direction. It will be evident that the terms rows and columns per se do not have an effect on the operation of the detector system. In the detector system of the example shown in FIG. 3, the detector cells in the first column from the left in the Figure have a width of 5 mm whereas those in the second and the third column have a width of 2 mm, those in the fourth and the fifth column have a width of 1 mm, those in the sixth and the seventh column have a width of 2 mm and those in the eighth column have a width of 5 mm. These widths are the dimensions in the transverse directions over which the individual detector cells are essentially sensitive to X-rays which have traversed the patient to be examined and reach the detector system. In the present example all detector cells have substantially the same dimensions in the longitudinal direction, i.e. along the columns. The detector cells in a column constitute the detector groups of detector cells having essentially the same effective cross-sections. For example, the seventh column constitutes a detector group 4 of detector cells having a width of 2 mm.

The shading in FIG. 3 indicates which part of the detector system is shielded from X-rays by the X-ray collimator. FIG. 3 shows that when using the relevant adjustment of the X-ray collimator, a part of the first column of detector cells which has a width of approximately 3 mm is shielded, so that a part of a width of approximately 2 mm of the detector cells in the first column can be reached by the X-rays. Furthermore, a part of a width of approximately 3 mm of the eighth column of detector cells is shielded, so that a part having a width of approximately 2 mm can be reached by the X-rays. Using this adjustment and this architecture of the detector system, detector groups having a width of 2 mm are formed: the parts of the first and the eighth column that can be reached by X-rays, and the detector cells in the second and the third, the sixth and the seventh column. Furthermore, the fourth and the fifth column together also act as a detector group having an effective width of 2 mm by combination of the signals from detector cells in the fourth and the fifth column in the same row. It is thus achieved that the computer tomography device according to the invention enables simultaneous measurement of density profiles of seven parallel slices 16 with a spatial resolution of approximately 2 mm in the transverse direction.

Figure 4:
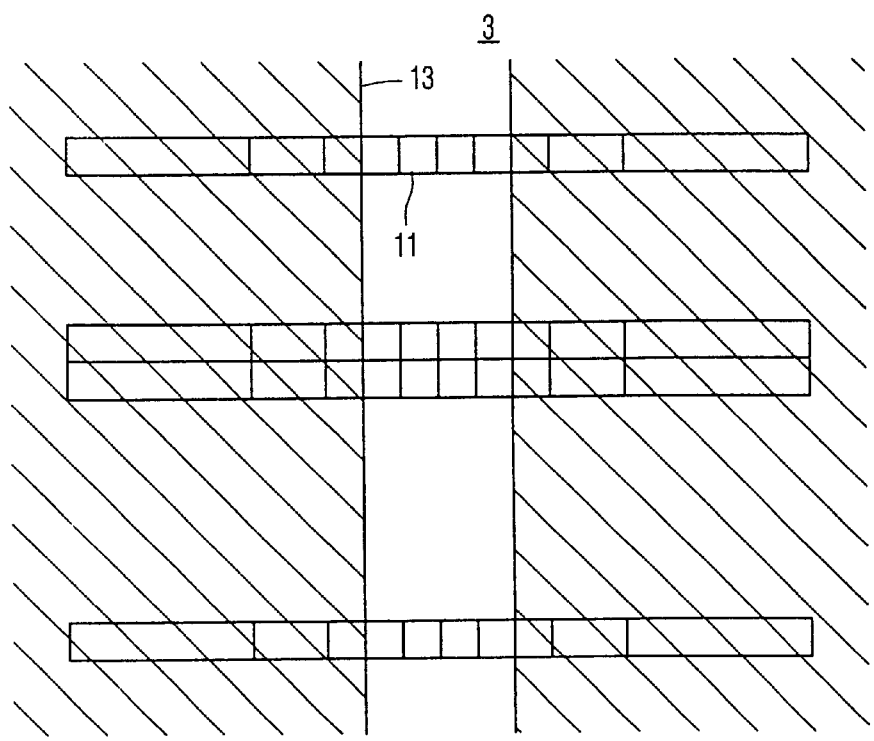

FIG. 4 is a diagrammatic view, looking in the direction from the X-ray source, of the detector system of the computer tomography device according to the invention while using a different adjustment of the X-ray collimator. The X-ray collimator is now adjusted in such a manner that the detector cells in the first, the second, the seventh and the eighth column are shielded, whereas the detector cells in the fourth and the fifth column can be reached by X-rays and a part of a width of 1 mm of the detector cells in the third and the sixth column is shielded so that a part of a width of 1 mm of the detector cells in the third and the sixth column can be reached by the X-rays. Using the adjustment shown in FIG. 4 and the relevant architecture of the detector system, four detector groups having an effective width of 1 mm can be formed, enabling simultaneous measurement of density profiles of four parallel slices of the patient with a spatial resolution of approximately 1 mm in the transverse direction. The profiles derived from the four parallel slices are referred to as "non-overlapping".

All references cited herein are incorporated herein by reference in their entirety and for all purposes to the same extent as if each individual publication or patent or patent application was specifically and individually indicated to be incorporated by reference in its entirety for all purposes.

What is claimed is:

1. A device comprising:
    an X-ray source of emitting an X-ray beam,
    a detector system for picking up density profiles of cross-sections of an object to be examined, and
    an X-ray collimator for spatially limiting the X-ray beam in the longitudinal direction, wherein the detector system includes a plurality of X-ray-sensitive detector elements which are arranged in a two-dimensional pattern, in which (i) detector elements in different positions along a transverse direction, parallel to the cross-sections, have substantially the same effective cross-section, (ii) whereas at least some of the detector elements in different positions along a longitudinal direction, transversely to the cross-sections, have different effective cross-sections, and (iii) substantially equal surface areas of detector groups, consisting of detector elements and/or parts of detector elements situated along the transverse direction, which detector elements can be reached by the limited X-ray beam to define several effective slice widths,
    wherein the density profiles of cross-sections of an object to be examined are non-overlapping at different values of the spatial resolution.

2. A computer tomography device as claimed in claim 1, wherein the X-ray collimator can be adjusted so as to adjust the limiting of the X-ray beam in the longitudinal direction, and wherein separate detector groups correspond to separate adjustments of the X-ray collimator.

3. A device as claimed in claim 1, wherein the detector allows for more than two distinct resolution modes.

4. A device as claimed in claim 3, wherein the detector detects density profiles of cross-sections of an object to be examined in all resolution modes.

5. A method for measuring non-overlapping density profiles comprising:

irradiating an object with X-rays from an X-ray source;

spatially limiting the X-rays in the longitudinal direction to define one of several effective slice widths;

detecting the X-rays in a two-dimensional pattern in at least two resolution modes constituting at least a high mode and a low mode; and generating non-overlapping density profile measurements from the detected X-rays from either of the at least two resolution modes.

6. The method of claim 5, wherein the at least two resolution modes have a plurality of resolution settings.

* * * * *